United States Patent [19]

Dent et al.

[11] 4,346,071

[45] Aug. 24, 1982

[54] REHYDRATED SILICA GEL DENTIFRICE ABRASIVE

[75] Inventors: Anthony L. Dent, Bala Cynwyd; M. Robert Derolf, Pottstown, both of Pa.; Elliot P. Hertzenberg, Wilmington, Del.

[73] Assignee: PQ Corporation, Valley Forge, Pa.

[21] Appl. No.: 186,083

[22] Filed: Sep. 11, 1980

Related U.S. Application Data

[63] Continuation-in-part of Ser. No. 90,167, Nov. 1, 1979, abandoned.

[51] Int. Cl.$^3$ ............................................... A61K 7/16
[52] U.S. Cl. ...................................................... 424/49
[58] Field of Search ...................................... 424/49-58

[56] References Cited

U.S. PATENT DOCUMENTS 4,153,680  5/1979  Seybert .................................. 424/49

*Primary Examiner*—Shep K. Rose
*Attorney, Agent, or Firm*—Ernest G. Posner; J. S. Stephen Bobb; Fred C. Philpitt

[57] ABSTRACT

Silicas that provide improved abrasive action when incorporated in dentifrice compositions can be prepared by dehydrating a silica hydrogel to a low water content and then reintroducing water to gel. The silica hydrogel is prepared by neutralizing a sodium silicate with an acid. This hydrogel is dried by any convenient method so that the gel contains about 15% water or less. This dried gel is rehydrated to about 30% or more. The rehydrated gel provides improved abrasion values over the prior art xerogels and hydrogels.

4 Claims, No Drawings

REHYDRATED SILICA GEL DENTIFRICE ABRASIVE

This application is a continuation in part of our co-pending patent application Ser. No. 090,167, filed on Nov. 1, 1979 now abandoned.

BACKGROUND OF THE INVENTION

This invention is concerned with dentifrice abrasives. In particular, it involves an improved silica abrasive.

Modern dentifrice compositions contain numerous components that have various therapeutic and cosmetic functions. Most of these compositions contain an abrasive cleansing agent which aids in the removal of adherent deposits on the teeth. Particulate matter of specific hardness and certain particle size, shape and structure are utilized as such abrasives. These particles must also be compatible with other toothpaste ingredients and safe for repeated human use. Abrasives that are described in the patent literature and have found commercial application include silica xerogels, hydrated silicas, hydrated aluminas, calcium carbonate, dicalcium phosphate (anhydrous and dihydrate), calcium pyrophosphate, and insoluble sodium metaphosphate. These agents are usually 2 to 30 micrometers ($\mu$m) in size. Products of about 10 $\mu$m appear to find the most commercial acceptance. Insoluble crystalline materials such as quartz have been found too abrasive for safe use on human teeth.

The use of silica xerogels is described in U.S. Pat. No. 3,538,230 to Pader & Weisner. This patent teaches that hydrogels prepared by acidifying a sodium silicate solution and then dried to a water content of 0.6 to 6% provide a xerogel that can be used as an abrasive especially for translucent and transparent toothpastes. U.S. Pat. No. 4,153,680 to Seybert teaches the use of a hydrogel as an abrasive for a dentifrice. This patent discloses that hydrogels prepared by neutralizing a sodium silicate solution and dried to between 17 and 32% water are effective abrasives. An important teaching of this patent is that the gel cannot be dried significantly below the level desired and then rehydrated to produce an effective product.

SUMMARY OF THE INVENTION

We have found that hydrated silica prepared by dehydrating a hydrogel with subsequent rehydration provides excellent abrasive action when formulated in dentifrice compositions. The silica is prepared by forming a hydrogel from a soluble silicate and acid, dehydrating the hydrogel from about 60 to 75% water to about 15% water or less and then rehydrating the silica to about 30% water or more. Our rehydrated silica is easily combined with other dentifrice components and provides the desired cleansing abrasiveness.

THE INVENTION

The rehydrated silica that we have found useful as an abrasive for dentifrices is prepared as follows. A hydrogel is prepared by neutralizing a soluble silicate solution. In general, mineral acids such as $H_2SO_4$ or $HNO_3$ are the neutralizing agents; however, acid-reacting salts and other materials are also useful. The neutralizing agent is mixed with the silicate solutions, and the mixture is allowed to gel. The solid gel is crushed before washing to remove the salts formed during neutralization and any other undesirable soluble impurities. The washed gel may be milled to the desired particle size before drying, or the milling may be subsequent to the drying. In any case, any convenient method of drying can be employed using temperatures of 40° to 500° C., preferably 50° to 350° C. The washed or dried gel can be milled in most mills capable of reducing the particle size of the gel to about 10 $\mu$m average particle size with a range of particles of 0.5 to 40 $\mu$m. The dried gel contains between 5 and 20% water. This gel is then treated with water to rehydrate the material. This treatment can be carried out in any convenient manner that does not result in hard agglomerates. The resulting free-flowing white powder is readily incorporated into dentifrice compositions to provide the desired cleansing abrasiveness.

We prefer to prepare rehydrated silica by the following method. A sodium silicate solution containing about 25% $SiO_2$ is mixed with sufficient $H_2SO_4$ at about 45% to produce a hydrosol at about 18% $SiO_2$ and with an excess of acid over that needed to completely neutralize the sodium in the silicate. The silicate and acid are combined using a mixing device wherein no localized concentration deformities are realized. We prefer to use a mixing nozzle as the mixing device. The hydrosol sets to a hydrogel which is crushed to a convenient size for washing. The crushed hydrogel is washed with water, adjusted to 3.5 pH with $H_2SO_4$ until a slurry of the gel has the desired final pH, such as, for example, 3.7 to 5.1. The gel now contains about 28% $SO_2$. The washed gel can be milled or dried as the next step. We prefer to use a fluid energy mill or an air swept hammer mill to reduce the particle size to 5 to 18 $\mu$m. While any convenient drying method can be used to reduce the water content from more than 65% to between 5 and 15%, we prefer that at least one portion or segment of the drying step be carried out at 150° to 350° C. Then water is added to the silica gel, usually in a device that agitates the material as the water is added and equilibrated. The final product is a fine white powder that contains 25 to 45% water and has a particle size of 5 to 18 $\mu$m. We prefer a product that contains 33 to 42% water. We determine water content by the loss on ignition (LOT), heating the sample to 1300° C.

Surprisingly, our rehydrated silica gels are more effective abrasives than hydrogels or xerogels, as determined in radioactive dentin abrasion tests. We tested a series of four hydrogels that had an average of about 31% water content. We tested a series of eleven xerogels which had an average water content of 9.86%. Both series of gels exhibited an average of 25.4 RDA units per gram of anhydrous silica. We also tested a series of nine rehydrated silica gels with an average water content of about 32%. Our material exhibited an average of 29.8 RDA units per gram of anhydrous silica. Calcium pyrophosphate was used as a standard of comparison for the RDA tests, and it was considered to have a value of 10.0 RDA units per gram of $Ca_2P_2O_7$.

Sufficient rehydrated silica can be used in dentifrice compositions to provide the required cleansing abrasion. In general, about 15 to 25% silica abrasive is included in a dentifrice. Since the rehydrated material has superior abrasive qualities, as little as 5% silica can be used. A dentifrice may contain as much as 80% silica abrasive. We prefer to use 10 to 65% of our rehydrated silica as the abrasive.

Numerous other ingredients constitute the balance of the dentifrice and provide various therapeutic, cosmetic and conditioning functions. Compounds containing stannous or calcium ions are added as therapeutic agents. Flourine compounds are also reputed to provide various benefits. Stannous fluoride is often used in various toothpastes. Humectants prevent hardness in the toothpaste and include, among others, glycerol, sorbitol and propylene glycol. Binders are important for the obvious reason, and include gum tragacanth, sodium carboxymethylcellulose, methylcellulose, hydroxyethylcellulose, propylene glycol alginates, Indian gum, Irish moss, carrageenan starch, agar agar and the like. Other ingredients include soaps and synthetic detergents, flavoring agents such as sweeteners, and oxygen releasers, buffers, preservatives and coloring agents.

The radioactive dentin abrasion (RDA) test indicates the abrasive properties of various materials and is carried out as follows. Eight radioactive teeth (neutron activation) are brushed 1000 times with various abrasives formulated into a standard paste. This standard paste consists of 6.25 g of the silica abrasive or 10.0 g of calcium pyrophosphate suspended in 50 ml of 0.5% carboxymethylcellulose in water. The entire thick slurry is used in the test brushing. These proportions translate into a silica content of about 12%, which is slightly below current commercial practice for toothpastes utilizing silica abrasives. The quantity of abraded tooth material is determined from the slurry, which contains radioactive material after the brushing. The results are compared to the calcium pyrophosphate standard which is assigned an RDA value of 100. Missouri Analytical Laboratories in St. Louis performed these tests for us. Hydrogels and xerogels as well as the rehydrated silicas of our invention were tested in this manner and the results are summarized in the following table.

TABLE I

Radioactive Dentin Abrasion Values for Silicas

| Silica Abrasive Agent | LOI (%) | RDA (units) | RDA (value corrected to anhydrous $SiO_2$) | RDA (RDA/g $SiO_2$) |
|---|---|---|---|---|
| hydrogel | 29.4 | 102 | 119 | 23.3 |
| hydrogel | 34.7 | 95 | 145 | 23.3 |
| hydrogel | 42.3 | 87 | 151 | 24.1 |
| xerogel | 6.7 | 132 | 141 | 22.6 |
| xerogel | 8.3 | 120 | 131 | 20.9 |
| xerogel | 7.8 | 139 | 151 | 24.1 |
| xerogel | 5.4 | 169 | 183 | 28.6 |
| rehydrated | 32.0 | 145 | 213 | 34.1 |
| rehydrated | 29.8 | 146 | 208 | 33.3 |
| rehydrated | 42.8 | 128 | 224 | 35.8 |
| rehydrated | 27.2 | 133 | 188 | 30.0 |

These results indicate clearly that rehydrated silica is a more effective abrasive than the hydrogel or xerogel. Rehydration of a dried silica gel must induce a structural change in the silica since the results for the hydrogels and xerogels are about equivalent, while the rehydrated materials have improved performance.

EXAMPLES

The following examples illustrate certain embodiments of our invention; they are not intended to establish the scope of our invention which is fully described in the specification and the claims. All proportions are in parts by weight (pbw) or weight percent (%) unless otherwise specified.

EXAMPLE 1

An initial hydrogel was prepared as follows. A commercially available sodium silicate solution was diluted so that it contained 25.4% $SiO_2$ and 7.89% $Na_2O$. A sulfuric acid solution was prepared to contain 45.6% $H_2SO_4$. These two solutions were mixed using a mixing nozzle so that the formation of localized gel was avoided. The flow rates were 3,000 cc/minute for the silicate and 1020 cc/minute for the acid. The temperature of the resulting sol was 51° C. The sol contained 18.9% $SiO_2$ and had a gel time of about 5 minutes. This gel was backwashed with deionized water adjusted to 3.5 pH until it had a slurry pH of 4.2. The washed gel had a $SiO_2$ content of 28.04% and a LOI of 71.95%. This material was milled to about 10 μm in a fluid energy mill.

EXAMPLE 2

A sample of the initial hydrogel prepared as described in Example 1 was dried for a short period of time at 150° C. to 9.6% water content, thereby forming a xerogel. This material was incorporated into a toothpaste and a RDA value of 110 (25 RDA/g of $SiO_2$) was obtained.

A second sample of the initial hydrogel was dried slowly at less than 100° C. to 7% water. The RDA value of this xerogel was 120 (20.6 RDA/g $SiO_2$).

A third sample was dried to about 10% at 150° C., then sufficient water to bring the LOI up to 32.0% was added and allowed to equilibrate while maintaining the gel in motion, providing a rehydrated silica. The RDA value was 145 (34.1 RDA/g $SiO_2$).

Still another sample of the initial hydrogel was partially dried at 105° C. The remainder of the water to 9.5% was removed at 310° C. This material was rehydrated to 34.0% water in the same manner as the previous sample. The RDA value was 122 (29.6 RDA/g $SiO_2$).

The results indicate that the rehydrated silicas are more efficient as toothpaste abrasives than xerogels.

We claim:

1. In the known multi-component dentifrice characterized in that silica gel is the abrasive cleansing agent the improvement consisting of a rehydrated silica gel abrasive cleansing agent which has a radioactive dentin abrasion (RDA) value of at least 30 units/g of anhydrous $SiO_2$ in a test wherein calcium pyrophosphate has an RDA value of 10 units per gram, said rehydrated silica constituting 5 to 80% of the weight of the dentifrice, having an average particle size of 5 to 18 μm, containing 25 to 45% by weight of water and being prepared by drying a silica hydrogel to a water content of 5 to 15% by weight and rehydrating said gel to 25 to 45% by weight of water.

2. The dentifrice of claim 1 wherein the rehydrated silica has an RDA value of about 30 to 35 units/g of anhydrous $SiO_2$.

3. The dentifrice of claim 2 wherein the rehydrated silica gel constitutes 10 to 65% by weight of the dentifrice composition.

4. The dentifrice of either of claims 1 or 3 wherein the dried silica gel is rehydrated to a water content of 33 to 42% by weight.

* * * * *